United States Patent [19]

Okada

[11] Patent Number: 5,211,548
[45] Date of Patent: May 18, 1993

[54] PERISTALTIC PUMP HAVING A MOTOR OVERLOAD PROTECTOR

[75] Inventor: Shigeru Okada, Fujinomoya, Japan

[73] Assignee: Terumo Kabushiki Kaisha, Japan

[21] Appl. No.: 867,061

[22] Filed: Apr. 10, 1992

Related U.S. Application Data

[63] Continuation of Ser. No. 558,051, Jul. 25, 1990, abandoned.

Foreign Application Priority Data

| Jul. 31, 1989 [JP] | Japan | 1-196515 |
| Jul. 31, 1989 [JP] | Japan | 1-196516 |

[51] Int. Cl.⁵ ............................. F04B 43/12
[52] U.S. Cl. ........................... 417/474; 604/153
[58] Field of Search .......... 417/474, 475; 604/153

[56] References Cited

U.S. PATENT DOCUMENTS

| 2,877,714 | 3/1959 | Sorg et al. | 417/474 X |
| 3,778,195 | 12/1973 | Bamberg | 417/474 |
| 4,493,706 | 1/1985 | Borsanyi et al. | 417/474 X |
| 4,861,830 | 12/1985 | Bradley | 417/474 |
| 4,725,205 | 2/1988 | Cannon et al. | 417/474 X |
| 4,728,265 | 3/1988 | Cannon | 417/474 X |
| 4,954,043 | 9/1990 | Irvin et al. | 417/474 X |

FOREIGN PATENT DOCUMENTS 56-113084 9/1981 Japan.
62-20182 2/1987 Japan.

Primary Examiner—Leonard E. Smith
Attorney, Agent, or Firm—Frishauf, Holtz, Goodman & Woodward

[57] ABSTRACT

A peristaltic pump in which a tube is stably supported by a platen so as to be stably collapsed by fingers during normal operation, whereas, when an excessively large collapsing force is exerted by one of the fingers, the excess portion of the force is absorbed without fail so as to realize a stable pumping operation. The level or ability for absorbing the excess collapsing force is easily adjustable in accordance with changes in conditions such as the elasticity of the tube and the size of the tube. The tube can be stably set in a proper position between the platen and a group of the fingers.

3 Claims, 6 Drawing Sheets

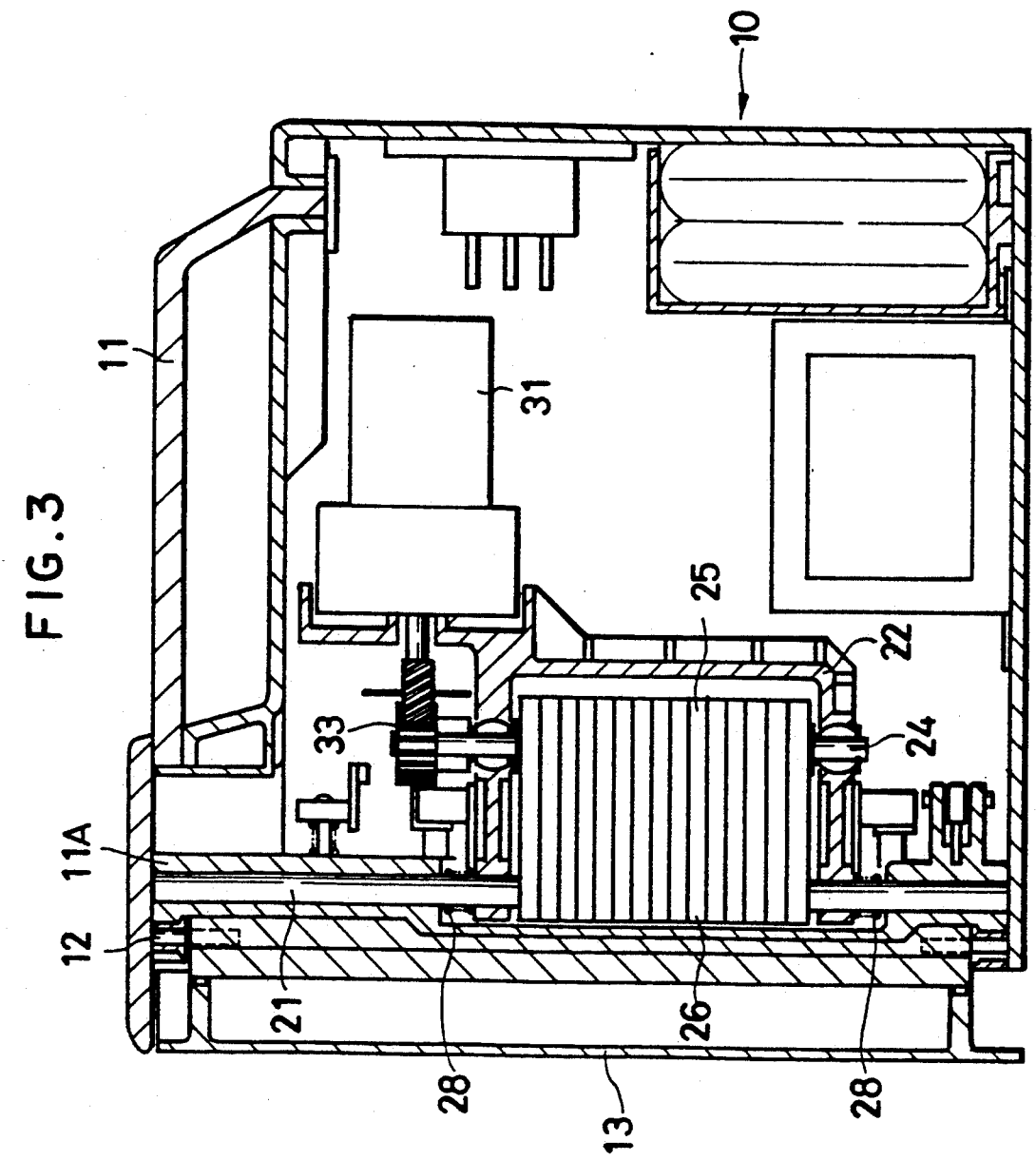

PERISTALTIC PUMP HAVING A MOTOR OVERLOAD PROTECTOR

This application is a continuation of application Ser. No. 07/558,051, filed Jul. 25, 1990, now abandoned.

BACKGROUND OF THE INVENTION

1. Field of the Invention

The present invention relates to a peristaltic pump suitable for use in, for example, transfusion.

2. Prior Art

Hitherto, various peristaltic pumps have been proposed as disclosed, for example, in Japanese Unexamined Patent Publication No. 56-113084. In general, a known peristaltic pump has a plurality of cams, a plurality of pressing fingers actuated by the cams so as to move between a retracted position and an operative position, and a platen opposing the pressing fingers so as to carry a tube therebetween. In operation, the pressing fingers are successively actuated to the operative position by the cams so as to collapse the tube, whereby a liquid in the tube is displaced and transported, while the elastic tube is allowed to restore when relieved from the pressing force so as to expand the liquid passage, thus performing a pumping action.

In the peristaltic pump of the type described, problems are caused such as damaging of the tube due to excessive pressing, unduly large load posed on the cam actuating device, and so forth, as a result of any dimensional errors caused during manufacture of the components such as the cams, pressing fingers and the platen, as well as insufficiency in the locating precision of these components. In order to obviate these problems, it has been proposed to provide an elastic support member on the back side of the platen opposite to the pressing fingers, so that any excessively large pressing force is absorbed by the elastic deformation of the supporting member thereby relieving and unburdening the platen.

When the platen is unburdened, the pressing force to be relieved acts only on a local point on the tube which is immediately under a certain pressing finger which has been set to the operative position. Therefore, during the unburdening, the platen does not always makes a translational movement. Namely, the platen may be moved at an inclination with respect to the plane of the group of pressing fingers. In such a case, the support of the tube on the platen is rendered unstable so as to impair the precision in control of the flow rate of the liquid during transfusion.

Under this circumstance, Japanese Unexamined Utility Model Publication No. 62-20182 discloses a peristaltic pump which is improved to eliminate the above-described problems concerning unburdening of the platen. In this improved peristaltic pump, any excessive force which would unduly collapse the tube is relieved not by a displacement of the platen but by elastic deformation of an elastic buffering portion of each pressing finger made of an elastic material. Thus, any excessive force applied to a pressing finger, which would otherwise be exerted on the tube, is effectively absorbed by the pressing finger itself.

PROBLEMS TO BE OVERCOME BY THE INVENTION (A) This improved peristaltic pump disclosed in Japanese Unexamined Utility Model Publication No. 62-20182, however, still suffers from the following problems ① and ②.

① Since the pressing finger is made of an elastic material and incorporates an elastic buffer portion, the pressing surface of the pressing finger tends to be displaced by the elastic reaction force produced by the tube. It is therefore difficult to stably collapse the tube and, hence, to attain a stable pumping action.

② Elastic buffer portions of different pressing fingers have different levels of absorption of excessive collapsing force and these levels are unadjustable. Therefore, when the elasticity or the size of the tube is changed to require a different levels of force absorption, replacement of all the pressing fingers or the whole pump is inconveniently required.

Accordingly, an object of the present invention is to provide a peristaltic pump in which a tube is constantly and stably held by a platen to allow the tube to be collapsed stably by pressing fingers under normal operating condition and, in the event of an application of any excessively large collapsing force, the excess of the collapsing force is absorbed without fail, thus realizing a stable pumping action.

Another object of the present invention is to provide a peristaltic pump which is improved to easily and freely adjust the level or ability to absorb excessive collapsing force in accordance with a change in the elasticity of the tube, size of the tube and other factors.

(B) Another problem encountered with the known peristaltic pump disclosed in Japanese Unexamined Patent Publication No. 56-113084 is not designed to stably set the entire part of the tube at proper position between the group of pressing fingers and the platen. This poses the following problems ① and ②.

① The tube winds in the space between the pressing fingers and the platen, so that the length of the portion of the tube pressed by each pressing finger may differ from the design length.

② The portion of the tube to be pressed by each pressing finger may be partly placed out of the area where the pressing force by the pressing finger is exerted.

These problems ① and ② make it immmpossible to press successive sections of the tube of a predetermined length, thus impairing the precision of the flow rate control.

Accordingly an object of the present invention is to provide a peristaltic pump which enables a tube to be stably set at a proper position between a group of pressing fingers and a platen.

DISCLOSURE OF THE INVENTION (A) To these ends, according to a first aspect of the present invention, there is provided a peristaltic pump comprising: a plurality of eccentric cams; a cam shaft carrying the cams and capable of driving the cams; a plurality of fingers adapted to be driven by the cams so as to press and collapse a tube: a platen arranged to oppose the group of fingers and capable of suppressing the movement of the tube in the direction of the pressing; a movable member relatively movable toward and away from the platen and incorporating the cams, the cam shaft and the pressing fingers; and urging means for urging the movable member towards the platen; wherein, when an excessively large pressing force is exerted on the tube by one of the pressing fingers, the movable member is moved away from the platen so as to reduce the pressing force exerted by the finger.

According to a second aspect of the present invention, there is provided a peristaltic pump of the first aspect, wherein the movable member is accommodated in a housing while the platen is secured to a door which is provided on the housing for movement between open and close positions.

According to a third aspect of the present invention, there is provided a peristaltic pump of the second aspect, wherein the urging means includes an urging member disposed between the movable member and the housing, and an adjusting member capable of adjusting the urging force of the urging member.

In the peristaltic pump of the first aspect of the invention, consecutive longitudinal sections of the elastic tube on the platen are successively collapsed as the successive fingers of the finger group are activated, namely, the position on the elastic tube where the collapsing force is exerted is progressively moved in the longitudinal direction of the tube, so that the liquid in the tube is displaced, whereas the portion of the tube relieved from the collapsing fore is allows to resume its original force by its elasticity so as to expand the liquid passage therein to suck a new portion of the liquid, whereby a pumping action is performed.

In the event that one of the pressing fingers is activated to exert an excessively large collapsing force, a correspondingly large elastic reaction force produced by the tube forces the movable member away from the platen against the urging force produced by the urging means. Consequently, the finger incorporated in the movable member is moved together with the movable plate away from the platen, i.e., in the direction opposite to the collapsing force exerted by the finger, whereby the excessive portion of the collapsing force exerted by the pressing finger is absorbed. In consequence, the tube is always stably held on the platen so that the tube is stably collapsed by the successive fingers during normal operation, whereas, when an extraordinarily large collapsing force is generated by a finger, the excessive portion of such a large collapsing force is absorbed without fail, whereby a stable pumping action is performed.

According to the second aspect of the invention, a compact construction of the peristaltic pump of the first aspect can be realized by virtue of the fact that the cams, fingers and the platen are housed in the housing through the door. Furthermore, the tube can easily be mounted in a proper position between the fingers and the platen through the door.

According to a third aspect of the present invention, in the peristaltic pump of the first or the second aspect, an adjusting member is provided for enabling an adjustment of the urging force produced by the urging member which backs up the movable member against the elastic reaction force produced by the tube. Thus, the level of force absorbed by a displacement of the pressing finger together with the movable member in the direction opposite to the collapsing force can easily be adjusted in accordance with a change in conditions or factors such as the elasticity of the tube, size of the tube, and so forth.

(B) To these ends, according to a fourth aspect of the present invention, there is provided a peristaltic pump comprising: a plurality of eccentric cams; a cam shaft carrying the cams and capable of driving the cams, a plurality of fingers adapted to be driven by the cams so as to press and collapse a tube; a platen arranged to oppose the group of fingers and capable of holding the tube between itself and the fingers; and a tube holder disposed between the fingers and the tube and/or between the platen and the tube and having tube holding means which is provided on the surface of the tube holder contactable with the tube and capable of holding the tube in a predetermined position.

According to a fifth aspect of the present invention, there is provided a peristaltic pump of the fourth aspect, wherein the tube holder includes a sheet-type elastic member having a recess-type tube holding means formed in the surface thereof contactable with the tube.

According to a sixth aspect of the present invention, there is provided a peristaltic pump of the fifth aspect, wherein the tube holder includes at least a pair of tube clamping poritons projecting into the recess.

According to a seventh aspect of the present invention, there is provided a peristaltic pump of the sixth aspect, further comprising clamping fingers capable of pressing the clamping portions so as to enable the clamping portions to clamp the tube.

According to an eighth aspect of the present invention, there is provided a peristaltic pump of the fourth, fifth, sixth, or seventh aspect, further comprising: a housing accommodating the cams, a cam shaft and the fingers and supporting a tube holder such that the tube holder is located at a position where it opposes the tube to be mounted; and a door supported on the housing for movement between open and close positions and carrying the platen such that the platen opposes the tube.

According to a ninth aspect of the present invention, there is provided a peristaltic pump of the fourth, fifth, sixth, seventh, or eight aspect, wherein the surface of the tube holder to be contacted by the tube is made of a silicon rubber having a large coefficient of friction, while the surface of the tube holder to be contacted by the fingers is made of a fluororesin having a small coefficient of friction.

According to a fourth aspect of the invention, consecutive longitudinal sections of the elastic tube on the platen are successively collapsed as the successive fingers of the finger group are activated, namely, the position on the elastic tube where the collapsing force is exerted is progressively moved in the longitudinal direction of the tube, so that the liquid in the tube is displaced, whereas the portion of the tube relieved from the collapsing fore is allows to resume its original force by its elasticity so as to expand the liquid passage therein to suck a new portion of the liquid, whereby a pumping action is performed.

In this fourth aspect, as well as in a fifth aspect, of the present invention, a tube is properly placed without any winding, by means of tube holding means on the tube holder, such that successive tube sections of the design length are placed in the pressing regions of the successive fingers, whereby the tube is correctly pressed by the successive pressing fingers at the successive sections so as to provide a high precision of control of the flow rate.

According to a sixth aspect of the present invention, the tube held by the tube holding means in the pump of the fifth aspect is clamped by a pair of clamp portions which are disposed at predetermined longitudinal position of the recess-type holding means, so that the successive sections of the tube can be properly located within the regions of the successive pressing fingers.

According to a seventh aspect of the present invention, the clamping portions of the tube holder in the sixth aspect of the invention are pressed by clamping fingers so that the locating precision of the tube is further enhanced.

According to an eighth aspect of the present invention, the cams, pressing fingers, the platen and the tube holder in the fourth to seventh aspects are accommodated in the housing through the door, whereby a compact pump can be realized. Furthermore, the tube can be set on the tube holder and, hence, can be mounted very easily in the right space between the group of fingers and the platen when the door is opened and closed.

According to a ninth aspect of the present invention, the tube holder in the fourth to eighth aspects of the present invention has a surface formed of a silicon rubber capable of stably holding the tube, while the surface of the tube holder to be contacted by the pressing fingers is formed of a fluororesin having a small coefficient of friction, thus minimizing the wear of the portions of the tube holder to be contacted by the pressing fingers.

BRIEF DESCRIPTION OF THE DRAWINGS

FIG. 3 is a longitudinal sectional view showing a critical portion of the peristaltic pump of FIG. 1;

BEST MODE FOR CARRYING OUT THE INVENTION

Figure 1:
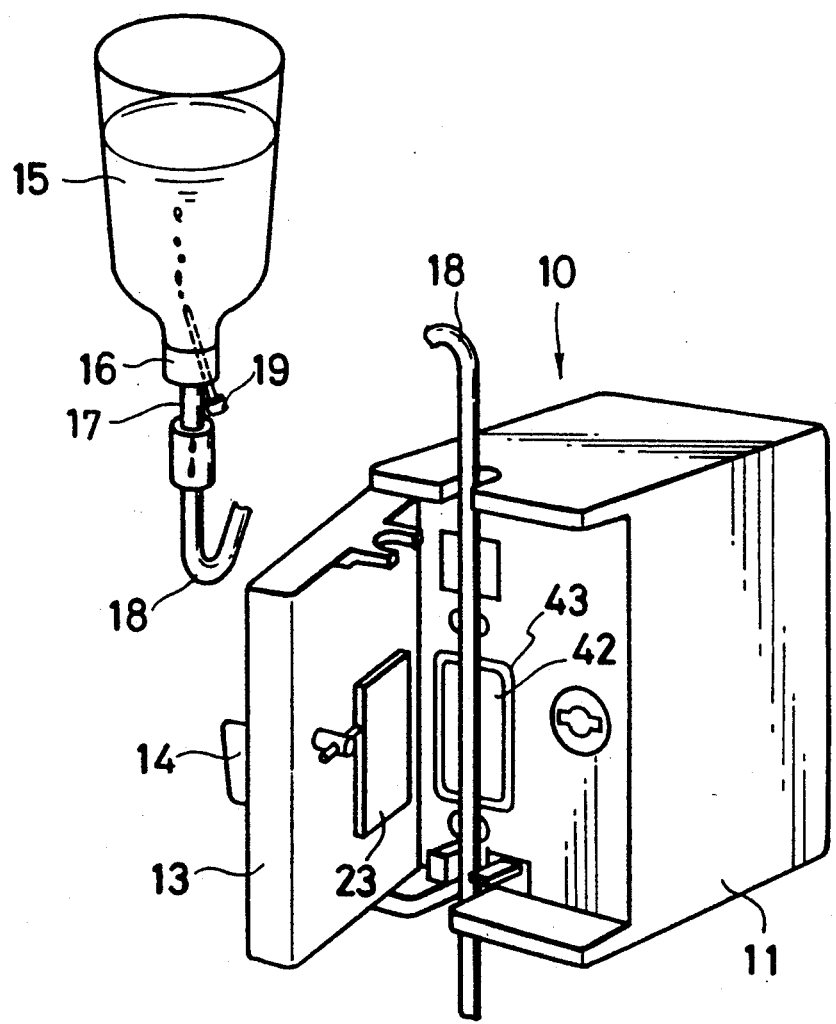
FIG. 1 is a schematic illustration of the whole of a peristaltic pump.
Figure 2A:
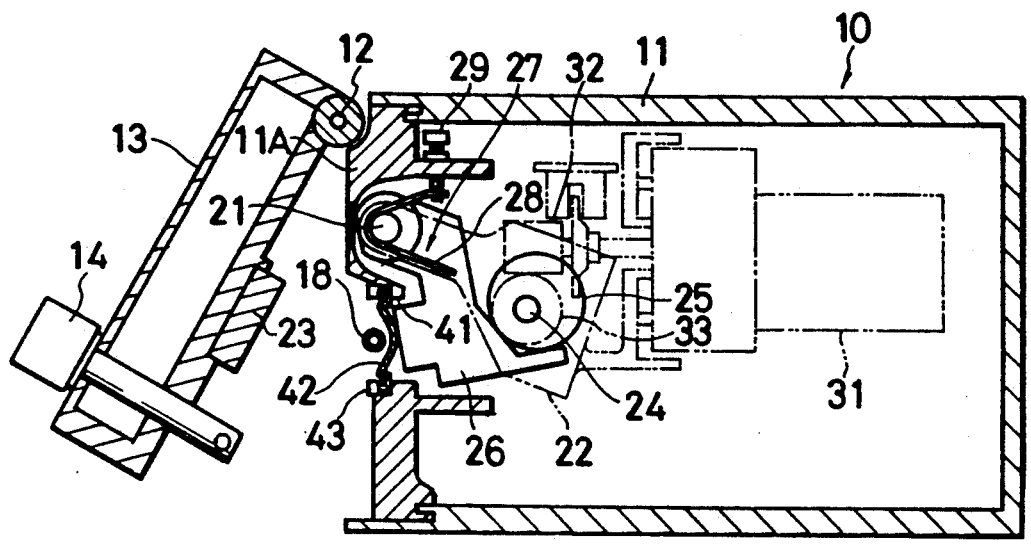
FIG. 2 is a sectional view showing a critical portion of the peristaltic pump of FIG. 1.
Figure 2B:
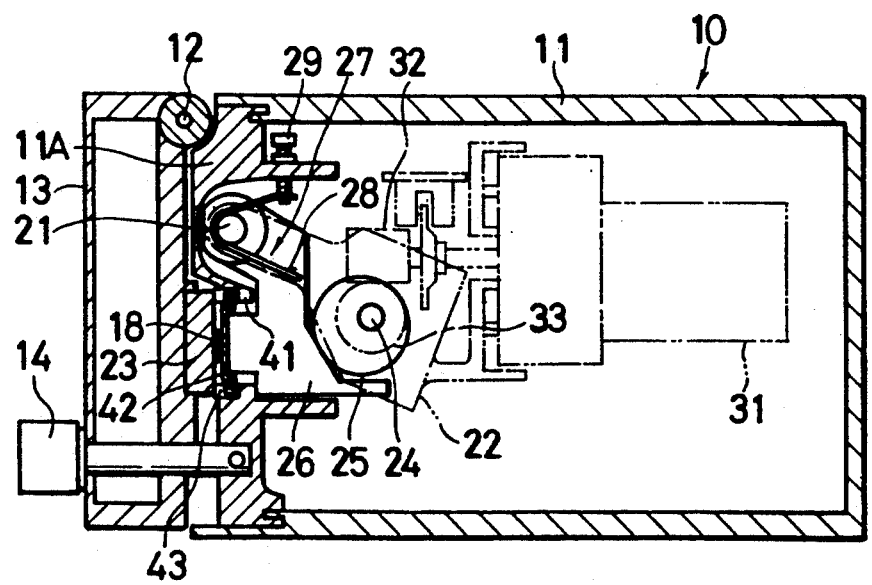

Referring to FIGS. 1 to 3, a peristaltic pump 10 has a housing 11 and a door 13 connected to the housing 11 through a door shaft 12 for pivotally movement between an open position and a close position. The door 13 is provided with a knob 14 which can be rotated to lock and unlock the door 13 in the close position.

The pump 10 is capable of effecting a pumping action on an intermediate portion of a tube 18 which is connected to a liquid guide needle 17 piercing a stop cock 16 of a transfusion vessel 15 shown in FIG. 1, so as to transfuse a liquid from the transfusion vessel 15 into the body of a patient. Numeral 19 denotes a ventilation needle.

Figure 4:
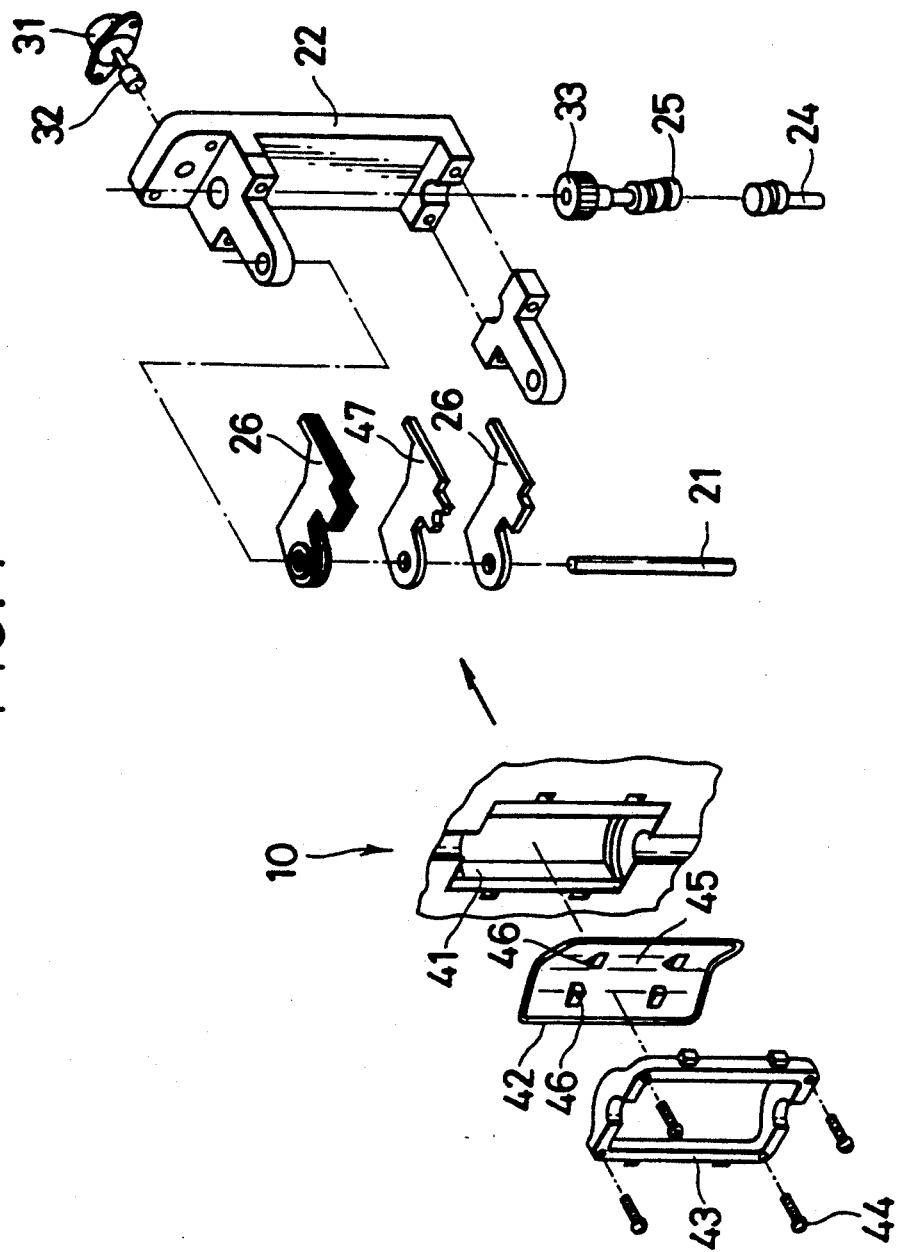
FIG. 4 is an exploded perspective view showing critical portions of the peristaltic pump of FIG. 1.

As shown in FIGS. 2 to 4, the pump 10 has a movable member 22 rockably carried by a pivot shaft 21 which is held at its both ends by brackets 11A fixed to the housing 11. The pump 10 also has a platen 23 supported on the door 13.

The movable member 22 is rockably supported by the pivot shaft 21 for rocking motion toward or away from the platen 23, and has a cam shaft 24 which extends in parallel with the pivot shaft 21. The movable member 22 also incorporates a plurality of eccentric cams 25 fixedly mounted on the cam shaft 24 along the length thereof, and a plurality of fingers 26 pivotally supported about the pivot shaft 21 and adapted to be pressed by the eccentric cams 25.

In this state, each finger 26 is adapted to be actuated by a corresponding eccentric cam 25 between a retracted position and an operative position. When the door 13 is closed, the platen 23 can be located so as to oppose the group 26A of fingers 26 so as to carry the tube 18 which is disposed between the platen 23 and the fingers 26. The fingers are successively set to the operative position by the operation of the successive eccentric cams 25 so that the position where the tube 18 is collapsed by the fingers is progressively moved in the longitudinal direction of the tube. It is to be noted that the tube is normally closed by at least one finger 26. The arrangement is such that, when one of the fingers 26 has commenced its backward movement beyond the maximum collapse position, the next finger keeps the tube in pressed condition so as to keep the internal liquid passage of the tube 18 until the above-mentioned finger 26 travels a distance large enough to open the portion of the internal liquid passage under this finger 26.

The pump 10 also has an urging means 27 which resiliently urges the movable member 22 toward the platen 23. The urging means can be composed of a torsion spring 28 (urging member) and an adjusting screw (adjusting member). In the illustrated embodiment, there are two torsion springs 28 which are arranged on the pivot shaft 21 at the respective sides of the movable member 22. Each torsion spring has one end engaging with the movable member 22, while the other end engages with the end of an adjusting screw 29 which is screwed to each bracket 11A fixed to the housing 11. In this state, the housing 11 carrying the brackets 11A to which the adjusting screws 29 are screwed and the platen 23 supported by the door 13 locked in the close position on the housing 11 are immovable relative to each other. Consequently, the torsion springs 28 act between the movable member 22 and the platen 23. The adjusting screws 29 can be driven into and out of threaded holes formed in the brackets 11A so as to adjust the urging forces produced by the torsion springs 28.

The pump 10 also has a drive motor 31 fixed to the movable member 22 and having an output shaft carrying a worm gear 32 meshing with a worm wheel 33 which is fixed to one end of the cam shaft 24.

The arrangement is such that the cam shaft 24 is rotatingly driven by the drive motor 31 so as to rotate the eccentric cams 25 thereby activating successive fingers 26, whereby a pumping action is performed as explained before.

The peristaltic pump 10 of the present invention has a tube guide device as will be understood from the following description.

Figure 5A:
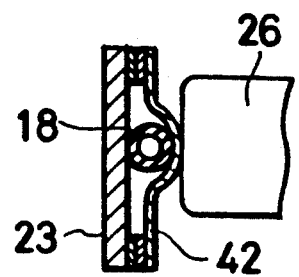
FIG. 5 is a schematic illustration of operation of pressing fingers of the peristaltic pump.
Figure 5B:
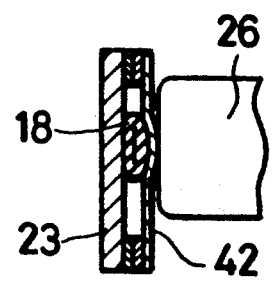

Namely, as shown in FIG. 4, each bracket 11A on the housing 11 has a pressing window 41 and a guide plate 42 for closing the pressing window 41. The guide plate 42 is fastened to the bracket 11A by means of screws 44 through a frame member 43 which presses the outer peripheral portion of the guide plate 42. As will be seen from FIGS. 2A and 2B, the guide plate 42 is provided with a tube guide groove 45 formed in the surface thereof which faces the platen 23 when the door 13 is locked in the close position on the housing 11 so as to set the tube 18. The guide plate 42 is made of a soft elastic material so as not to impede the collapsing action of the fingers 26 when the successive fingers are set to the operative position for collapsing the tube 18. Therefore, as shown in FIG. 5A, the tube 18 is received in and guided by the guide groove 45 of the guide plate 42 so as to be correctly set without winding, in such a manner that successive tube sections of a predetermined length are correctly located in the pressing regions of the successive fingers. Consequently, the tube is stably collapsed by the successive fingers as these fingers are set to the operative position, whereby a higher precision of control of the liquid flow rate can be obtained, as will be seen from FIG. 5B.

As shown in FIG. 4, the guide plate 42 is provided with two pairs of clamping portions 46 spaced in the longitudinal direction of the guide groove 45 and formed onopposing walls of the guide groove 45 so as to project into the guide groove 45 thereby to clamp the tube 18. The pair of clamping portions 46 of each pair oppose each other so as to define therebetween a gap substantially equal to the outsidediameter of the tube 18. Thus, the clamping portions 46 serve to locate the tube 18 in the groove 45 more precisely within the region where the collapsing forces are exerted by the successive fingers 26.

Figure 6:
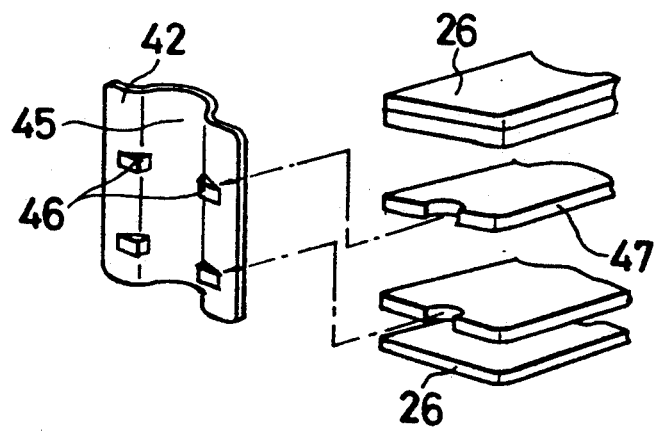
FIG. 6 is a schematic illustration showing a guide plate and clamping fingers in the peristaltic pump.
Figure 7:
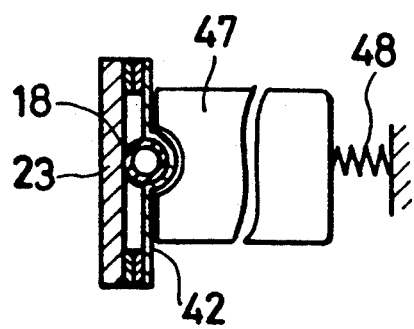
FIG. 7 is a schematic illustration of operation of pressing fingers.

As shown in FIGS. 6 and 7, the peristaltic pump of the present invention has a plurality of clamping fingers 47 each of which are disposed at positions corresponding to the respective pairs of opposing clamping portions 46 on the guide plate 42 and between two adjacent pressing fingers 26. Each clamping finger 47 is configured to have a recess which surrounds the portion of the guide plate 42 forming the guide recess 45, so as not to collapse the tube 18 and so as to press the clamping portions 46. As schematically shown in FIG. 7, each clamping finger 47 is urged towards the clamping portions 46 by means of a backup spring 48 acting between itself and the housing 11, thereby enhancing the locating effect of the clamping portions 46 for locating the tube 18.

The guide plate 42 is made of, for example, a rubber and the surface of the guide plate 42 opposite to the guide recess 45, i.e., the surface to be pressed by the fingers 26, is embossed so as to reduce the coefficient of friction, thereby suppressing friction due to contact with the fingers 26.

Figure 8:
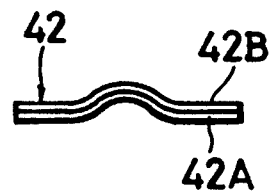
FIG. 8 is a schematic illustration of a guide plate.

As shown in FIG. 8, the guide plate 42 may be a composite member the surface of which contactable with the tube 18 is formed from a material having a large coefficient of friction, e.g., a silicon rubber 42A, so as to provide a stable support for the tube 18, while the surface thereof to be pressed by the fingers 26 is formed from a material which has a small coefficient of friction and, hence, exhibits a small tendency of wear, e.g., a fluororesin 42B.

The operation of the peristaltic pump having the described construction is as follows:

① The tube is set in the guide recess 45 formed in the guide plate 42 and carried by the platen 23 so as to be located in the correct position in the space between the group 26A of the pressing fingers 26 and the platen 23. In this state, the pressing fingers 26 are activated successively by the operation of corresponding cams so as to be brought into their operative positions, so that the position of the collapsed portion of the tube is progressively moved in the longitudinal direction of the tube 18. Consequently, the liquid in the internal liquid passage in the tube is displaced so as to be delivered into, for example, the body of a patient, while the portion of the tube relieved from the pressing force exerted by the pressing finger 26 resumes its original form due to its elasticity so that the internal passage is expanded again to suck a new portion of the liquid, whereby a pumping action is performed.

When one of the fingers 26 of the group 26A is actuated to exert an extraordinarily large force onto the tube 18, a correspondingly large elastic reaction fore produced by the tube serves to force the movable member 22 backward away from the platen 23, against the force of the urging means 27, so that the finger 26 incorporated in this movable member 22 is moved together with the movable member 22 away from the platen 23, in.e., away from the tube 18, thereby absorbing excess portion of the collapsing force exerted by the finger 26. Consequently, the tube 18 is always held by the platen 23 in quite a stable manner and is smoothly collapsed by the successive fingers 26 under normal operating condition. In the event that an extraordinarily large pressing force is applied by one of the fingers 26, the excessive portion of the collapsing force is absorbed without fail so as to protect the tube 18 and to ensure a stable pumping operation.

In addition, the tube 18 is received in and guided by the tube guide recess 45 formed in the guide plate 42 so that the entire portion of the tube is correctly set without wining, such that successive tube sections of a predetermined length are located in the successive areas where pressing forces are to be applied by the successive pressing fingers 26. Therefore, the tube is collapsed in quite a stable manner as the successive pressing fingers are set to operative positions, thus enhancing the precision in the control of the flow rate of the liquid under transfusion.

② The major and essential portions including the eccentric cams 25, pressing fingers 26 and the platen 23 which are housed in the housing 11 by means of the door 13 so that a compact construction of the pump 10 is obtained. In addition, it is possible to set the tube 18 in the correct position between the group 26A of the pressing fingers 26 and the tube 18 very easily by the opening and closing action of the door 13.

③ The cam driving device of the pump is mounted on the movable member 22 which incorporates the eccentric cams 25, so that the actuating mechanism which operatively connects the eccentric cams 25 to the cam driving device can be set on the movable member 22, thus contributing to a simplification of the construction.

④ The urging force produced by the torsion spring 18, which backs up the movable member 22 against the elastic reaction force produced by the tube 18 is adjustable by means of the adjusting screw 29. Thus, the ability of the pressing finger 26, which is displaceable together with the movable member 22 to absorb any excessive collapsing force, is adjustable without difficulty in accordance with changes in conditions such as the elasticity of the tube 18, size of the tube 18 and so forth.

⑤ The pairs of clamping portions, which are provided at predetermined positions along the length of the guide recess 45 in the guide plate 42, effectively clamp the tube 18 so as to locate the tube 18 more precisely in the region where the collapsing pressing forces are exerted by the successive pressing fingers 26.

⑥ By pressing the clamping portions 46 on the guide plate 42 by means of the clamping fingers 47, it is possible to enhance the locating effect of the clamping portions 46 for locating the tube 18.

(7) A compact construction of the pump 10 is obtained by virtue of the use of the housing 11 with the door 13 for accommodating the eccentric cams 25, pressing fingers 26 and the platen 23. In addition, it is possible to easily set the tube 18 in the guide plate 42 when the door is opened and closed, whereby the tube 18 can be correctly located in the space between the group 26A of the pressing fingers 26 and the platen 23.

The guide plate 42 of the pump 10 serves to stably locate the tube 18 in the region where the collapsing forces are applied by the successive pressing fingers so as to enhance the precision of control of the flow rate of the liquid, and covers the pressing window 41 in the bracket 11A so as to prevent the liquid flowing in the tube 18 from accidentally coming into the mechanical portion of the pump. Consequently, contamination of the mechanism also is prevented.

Figure 9:
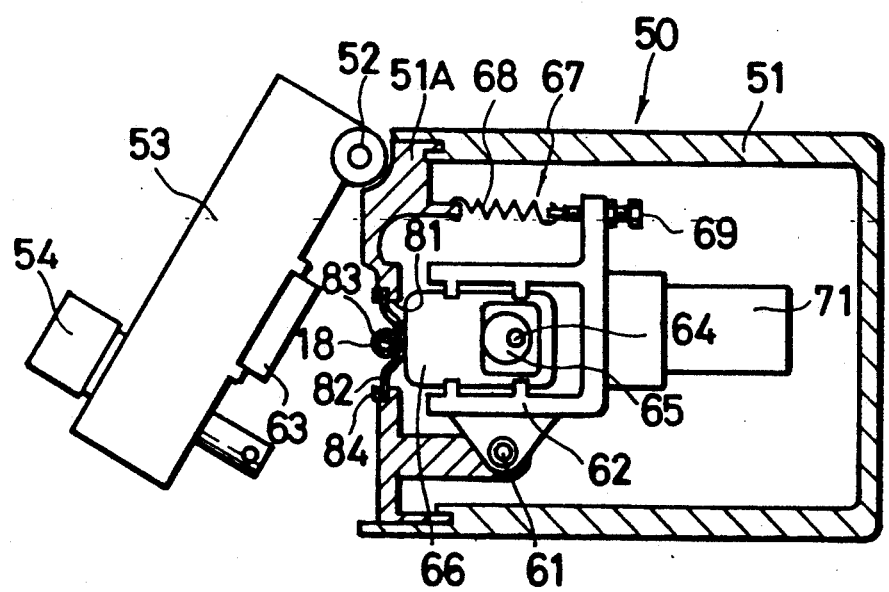
FIG. 9 is a cross-sectional view of another embodiment of the peristaltic pump in accordance with the present invention.

FIG. 9 shows a second embodiment of the peristaltic pump of the present invention. The peristaltic pump shown in FIG. 9 is different from the peristaltic pump of the first embodiment in that the fingers are arranged for linear movement with respect to the movable member, as will be understood from the following description.

Referring to FIG. 9, the peristaltic pump 50 of the second embodiment has, as is the case of the first embodiment, a housing 51, a door shaft 52, a door 53 and a knob 54.

The pump 50 also has a support shaft 61 which is carried at its both ends by a bracket 51A fixed to the housing 51. The support shaft 61 rockably carries a movable member 62. The pump 50 also has a platen 63 supported by the door 53.

The movable member 62 is supported for rocking motion around the support shaft 61 toward and away from the platen 63. The movable member 62 has a cam shaft 64 which extends in parallel with the support shaft 61 and incorporates a plurality of cams 65 fixedly carried by the cam shaft 64 and arranged along the length of the support shaft 61. The movable member 62 also incorporates a plurality of pressing fingers 66 which are adapted to be linearly actuated by the cams 65.

Thus, each of the pressing fingers 66 is movable between a retracted position and an operative position by the action of the associated cam 65. The platen 63 is adapted to be positioned so as to oppose the group 66A of fingers 66 so as to hold the tube 18 between itself and the pressing fingers 66. As the successive cams are operated, the associated fingers are set to the operative positions so that the position of the collapsed portion of the tube is progressively moved in the longitudinal direction of the tube.

The pump 50 further has an urging means 67 which urges the movable member 62 towards the platen 63. The urging means 67 is composed of a tensile spring 68 (urging member) and an adjusting screw 69 (adjusting member). The tensile spring 68 has one end retained by an end of the adjusting screw 69 which is screwed to the movable member 62 and the other end which is retained by the bracket 51A on the housing 51. The adjusting screw 69 can be driven into and out of the threaded hole in the bracket 51A so as to adjust the urging force produced by the tensile spring 68.

The pump 50 also has a drive motor 71 mounted on the movable member 62 and capable of driving the cam shaft 64 so as to rotate the cams 65 on the camshaft 64, thereby operating the pressing fingers 66 corresponding to these cams 65.

As in the case of the pump 10 of the first embodiment, the pump 50 has a guide plate 82 which is disposed to cover the pressing window 81 in the bracket 51A of the housing 51 and which is provided with a tube guide recess 83 for setting the tube 18. Numeral 84 denotes a frame.

The pump 50 having the described construction operates substantially in the same manner as the pump 10 of the first embodiment.

In the first embodiment as described, the movable member is supported for linear motion with respect to the housing.

EFFECT OF THE INVENTION

As has been described, according to the first to third aspects of the present invention, the tube is always held in a stable manner by the platen and is stably collapsed by the successive fingers under normal operating condition, whereas, in the event that an extraordinarily large force is applied, the excess portion of the collapsing force exerted by the pressing finger is effectively absorbed so as to ensure a stable pumping operation.

Furthermore, according to the first to third aspects of the invention, it is possible to easily adjust the level of the excess collapsing force to be absorbed, in accordance with a change in the conditions such as the elasticity of the tube, size of the tube, and so forth.

In addition, according to the fourth to ninth aspects of the invention, it is possible to stably set the tube in the right position between the group of pressing fingers and the platen.

What is claimed is:

1. A peristaltic pump comprising:
   a motor means;
   a plurality of eccentric cams;
   a cam shaft connected to be driven by said motor means for carrying and driving said plurality of eccentric cams;
   a plurality of fingers pivotally positioned along an axis of a pivot shaft, said plurality of fingers being pivotal about said axis of said pivot shaft and being adapted to be successively driven by said plurality of eccentric cams to pivot about said pivot shaft for pressing and collapsing a flexible tube in a given direction along said axis;
   a platen arranged to oppose said plurality of fingers for suppressing a movement of said flexible tube in the given direction;
   said plurality of fingers being urged to press said flexible tube by said plurality of eccentric cams and said cam shaft, said plurality of fingers respectively being pivotally mounted for pivotal movement toward and away from said platen; and
   urging means positioned coaxially with said axle of said pivot shaft for urging said plurality of fingers toward said platen up to a predetermined position.

2. A peristaltic pump as set forth in claim 1, wherein said urging means comprises an adjusting member for preventing said urging means from providing an excessive urging force on said flexible tube by said plurality of fingers.

3. A peristaltic pump as set forth in claim 1, further comprising a guide member for stably positioning said flexible tube within a pressing region.

* * * * *

UNITED STATES PATENT AND TRADEMARK OFFICE
CERTIFICATE OF CORRECTION

PATENT NO. : 5,211,548

DATED : May 18, 1993

INVENTOR(S) : OKADA, Shigeru

It is certified that error appears in the above-identified patent and that said Letters Patent is hereby corrected as shown below:

Title page:

```
Section [56] References Cited,
    Under "U.S. PATENT DOCUMENTS"
        Add --4,758,228    7/1988    D. Williams--.
        Change "4,861,830" to --4,561,830--.

Under "FOREIGN PATENT DOCUMENTS"
        Add --0,283,614    9/1988    EPA
             0,239,769   10/1987    EPA
             0,239,255    9/1987    EPA--.

Section [73] Assignee
    before "Japan"  insert  --Tokyo--.
```

Signed and Sealed this

Twentieth Day of December, 1994

*Attest:*

BRUCE LEHMAN

*Attesting Officer*     *Commissioner of Patents and Trademarks*